US007741624B1

(12) United States Patent
Sahadevan

(10) Patent No.: US 7,741,624 B1
(45) Date of Patent: Jun. 22, 2010

(54) SINGLE SESSION INTERACTIVE ULTRA-SHORT DURATION SUPER-HIGH BIOLOGICAL DOSE RATE RADIATION THERAPY AND RADIOSURGERY

(76) Inventor: Velayudhan Sahadevan, 200 Granville Ave., Beckley, WV (US) 25801

( * ) Notice: Subject to any disclaimer, the term of this patent is extended or adjusted under 35 U.S.C. 154(b) by 192 days.

(21) Appl. No.: 12/151,014

(22) Filed: May 3, 2008

(51) Int. Cl.
*A61N 5/06* (2006.01)
*G01J 5/02* (2006.01)

(52) U.S. Cl. .............. 250/494.1; 250/492.1; 250/492.3; 250/341.7; 378/65; 600/427; 600/9

(58) Field of Classification Search .............. 250/336.1, 250/339.06, 340, 341.7, 362, 363.01, 363.02, 250/370.08, 370.09, 492.1, 492.3, 493.1, 250/494.1; 378/64, 65, 101, 108, 119, 145, 378/137, 138, 901; 600/9, 10, 427; 128/897, 128/920
See application file for complete search history.

(56) References Cited

U.S. PATENT DOCUMENTS

| | | | | |
|---|---|---|---|---|
| 5,161,546 A | * | 11/1992 | Bronn | 128/897 |
| 5,190,516 A | * | 3/1993 | Bronn | 600/1 |
| 5,452,720 A | * | 9/1995 | Smith et al. | 600/427 |
| 5,528,652 A | * | 6/1996 | Smith et al. | 378/65 |
| 5,866,914 A | * | 2/1999 | Jones | 250/505.1 |
| 7,221,733 B1 | * | 5/2007 | Takai et al. | 378/65 |
| 2002/0094119 A1 | * | 7/2002 | Sahadevan | 382/132 |
| 2003/0123609 A1 | * | 7/2003 | Manske | 378/65 |
| 2004/0197264 A1 | * | 10/2004 | Schwarz et al. | 424/1.11 |
| 2005/0058245 A1 | * | 3/2005 | Ein-Gal | 378/65 |
| 2007/0040127 A1 | * | 2/2007 | Brahme et al. | 250/389 |
| 2009/0186060 A1 | * | 7/2009 | Hainfeld et al. | 424/422 |

* cited by examiner

*Primary Examiner*—Bernard E Souw

(57) ABSTRACT

A medical accelerator system consisting of coplanar and non-coplanar beams, on line magnetic resonance anatomic and functional imaging and cone beam computed tomographic imaging for single session image guided all field simultaneous radiation therapy and radiosurgery is provided. This system enables single session simulation, field-shaping block making, treatment planning, dose calculations and treatment of tumors. The radiation exposure time to the tumor and the normal tissue is reduced to a few seconds to less than a minute. In filed intensity modulated radiation is rendered by combined divergent and pencil beam, multiple smaller fields within a larger field, selectively varying beam's energy, dose rate and beam weight. Since all the treatment fields are treated simultaneously the dose rate at the tumor site is the sum of each of the converging beam's dose rate at depth. This super-high biological dose rate impairs the lethal and sublethal damage repair.

21 Claims, 13 Drawing Sheets

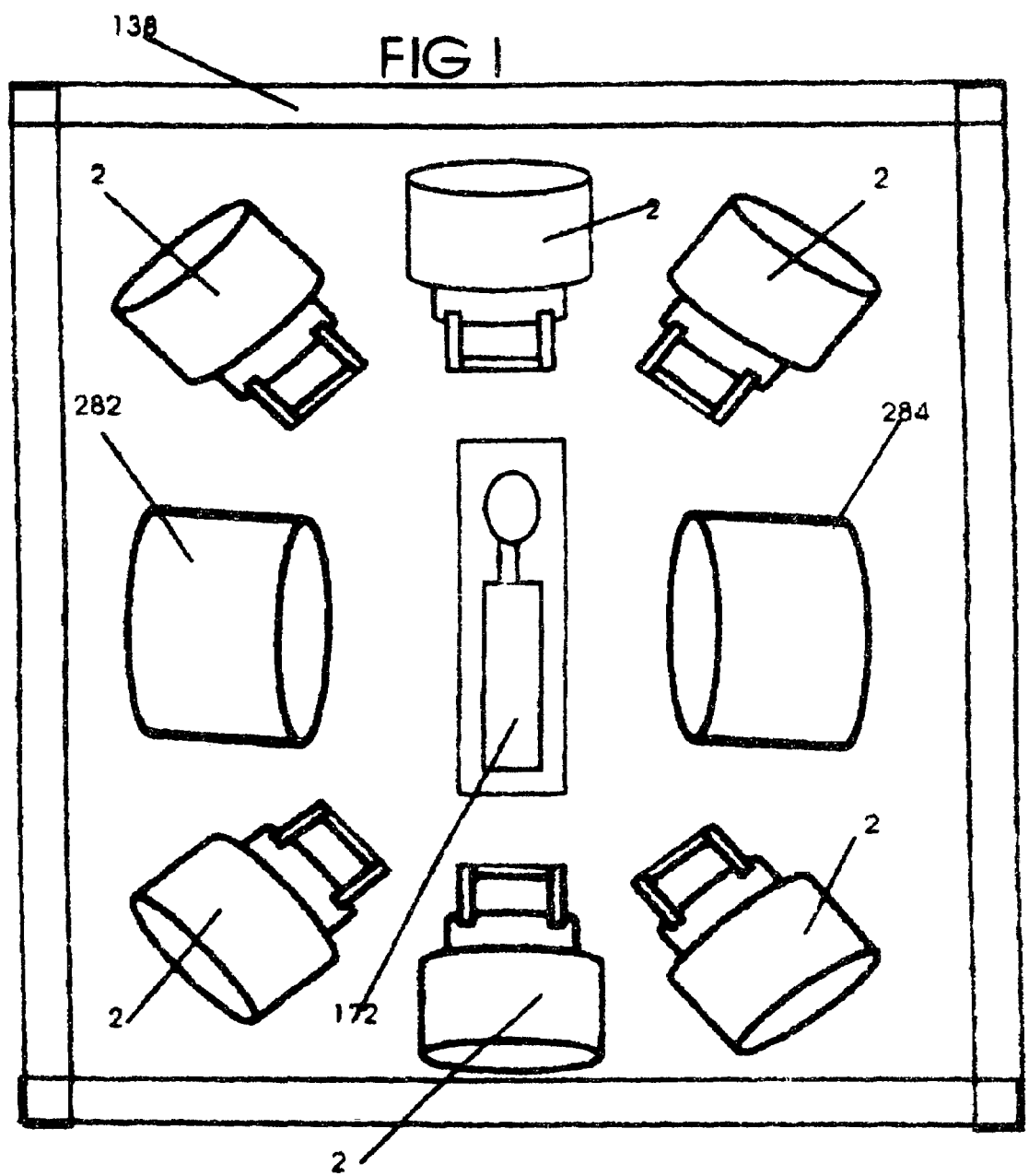

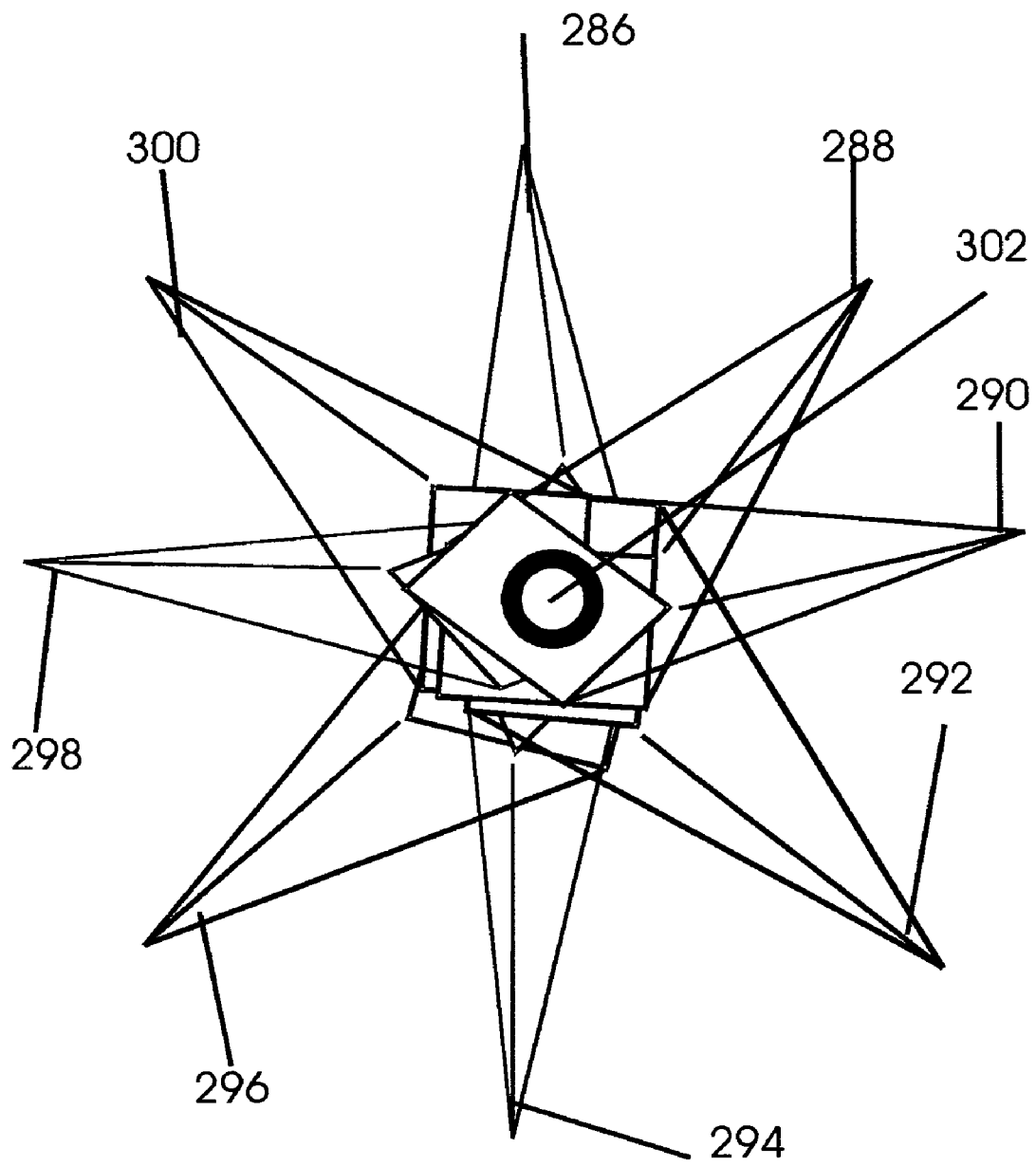

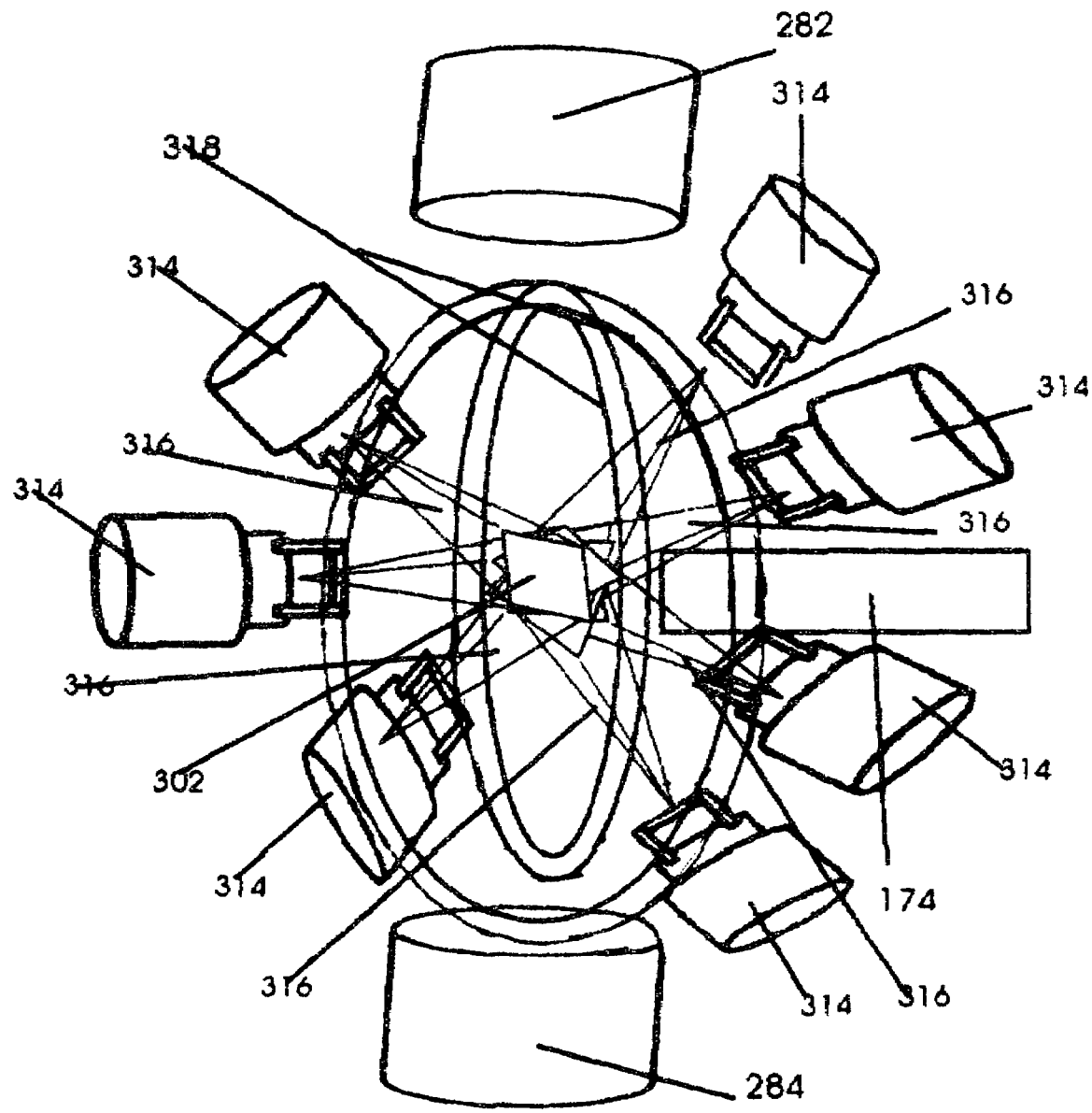

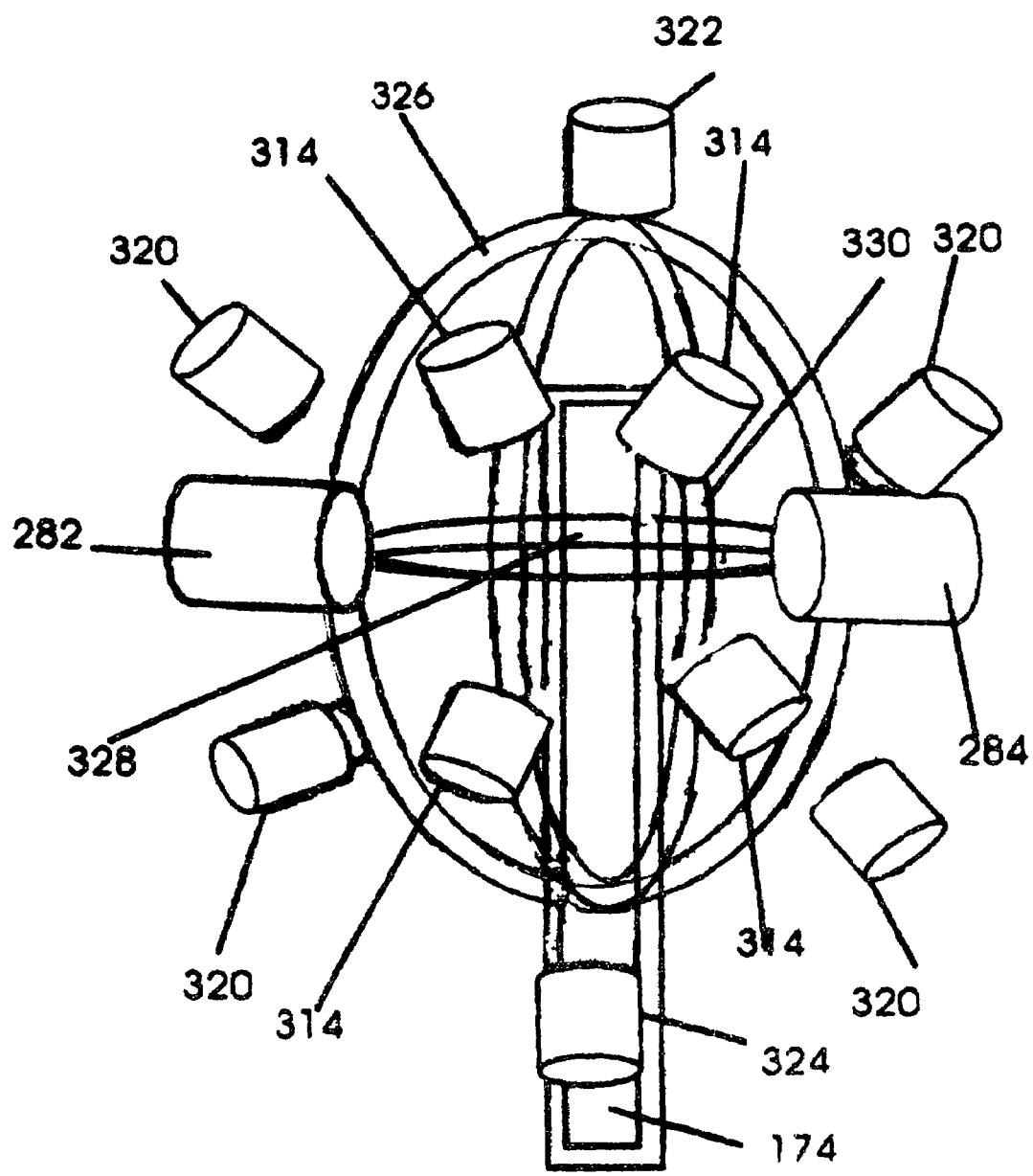

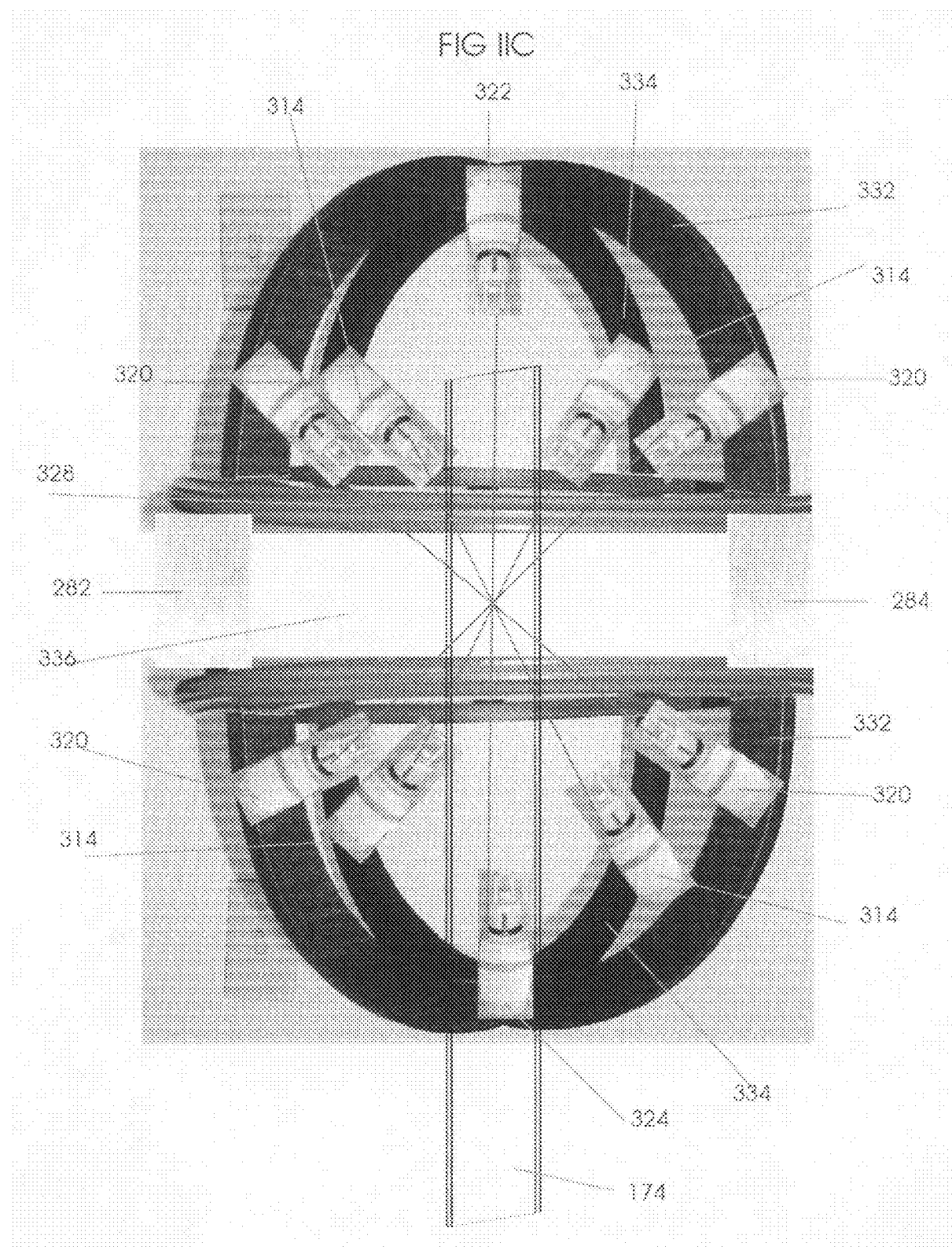
FIG IIC

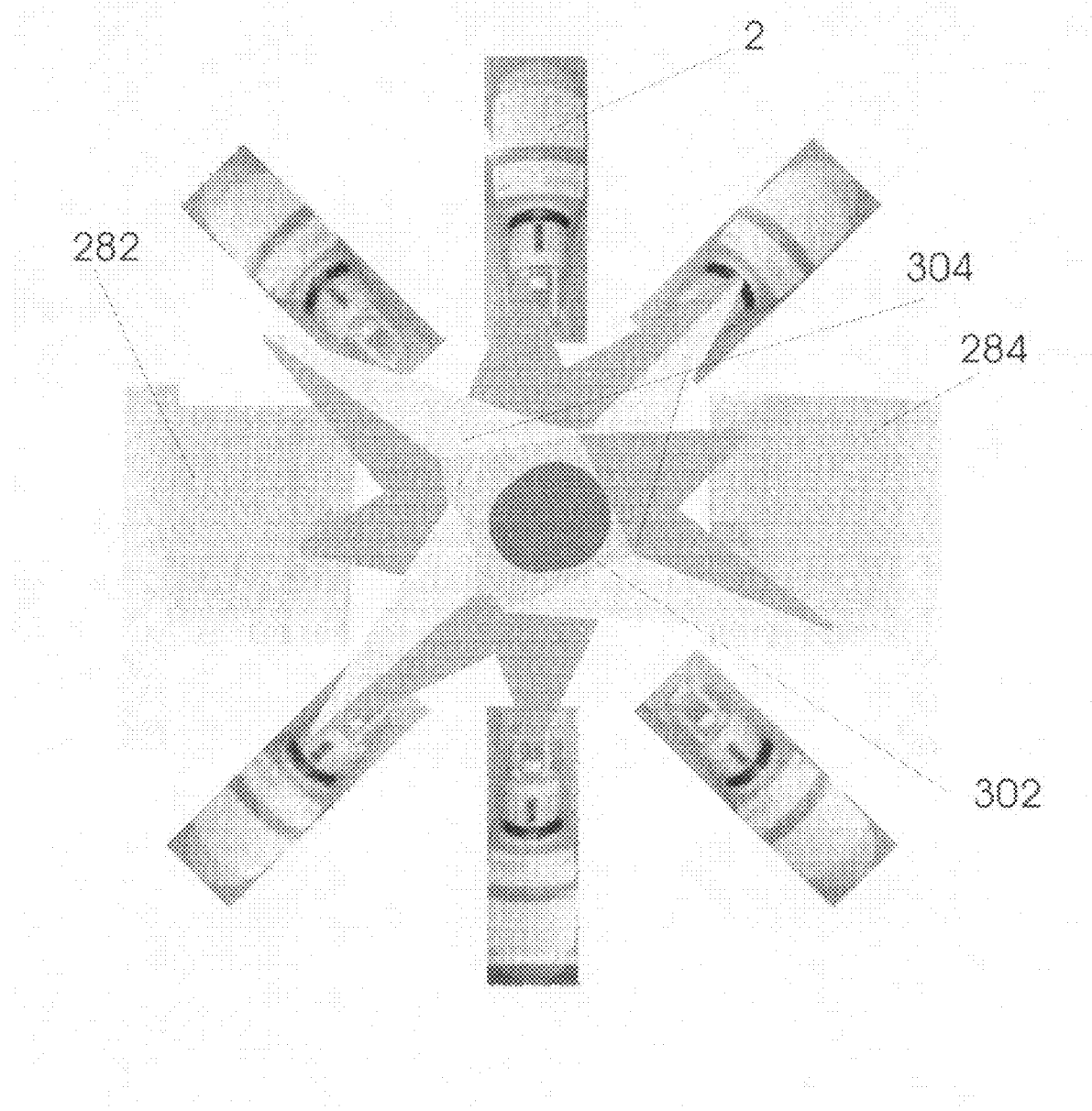

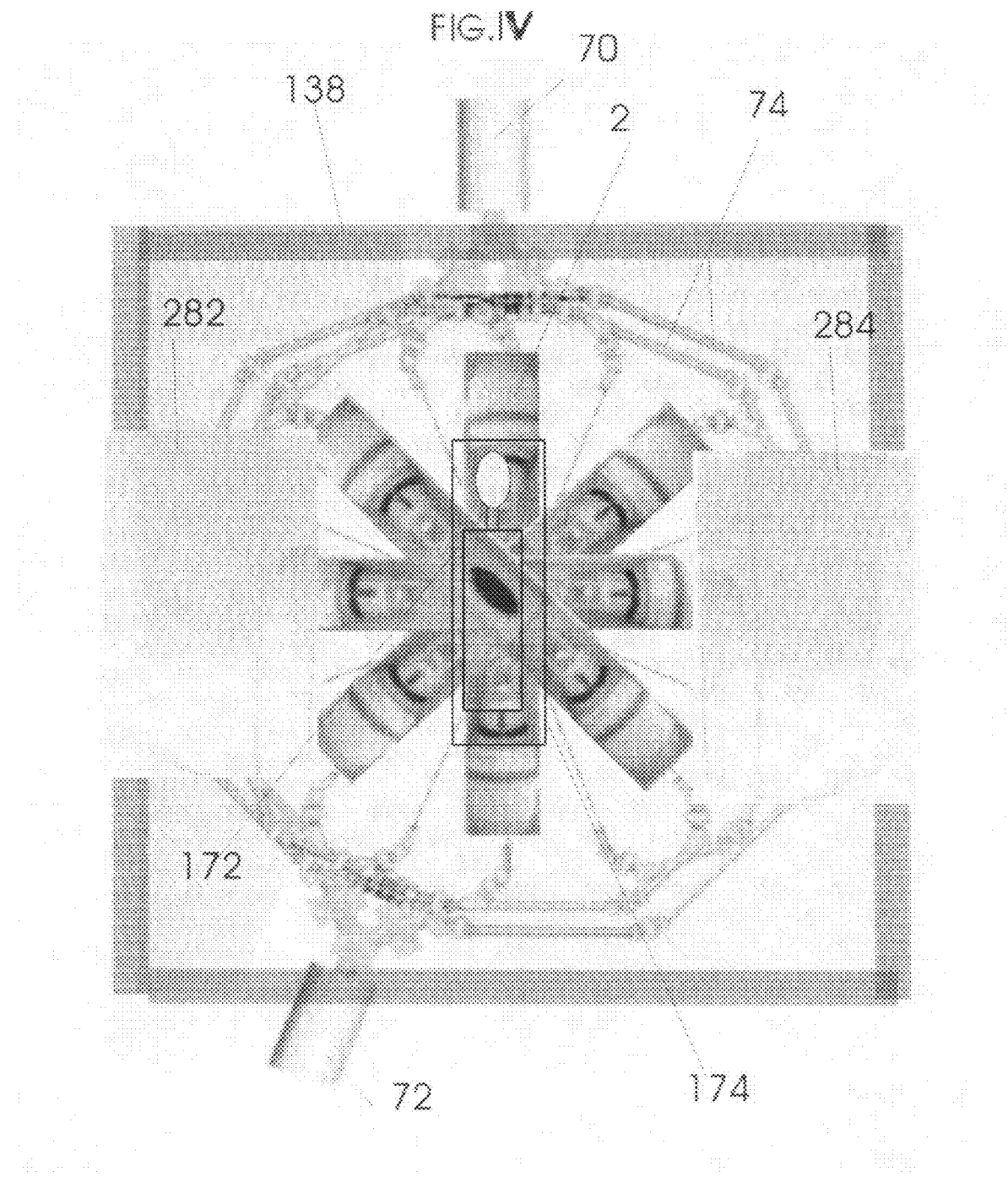

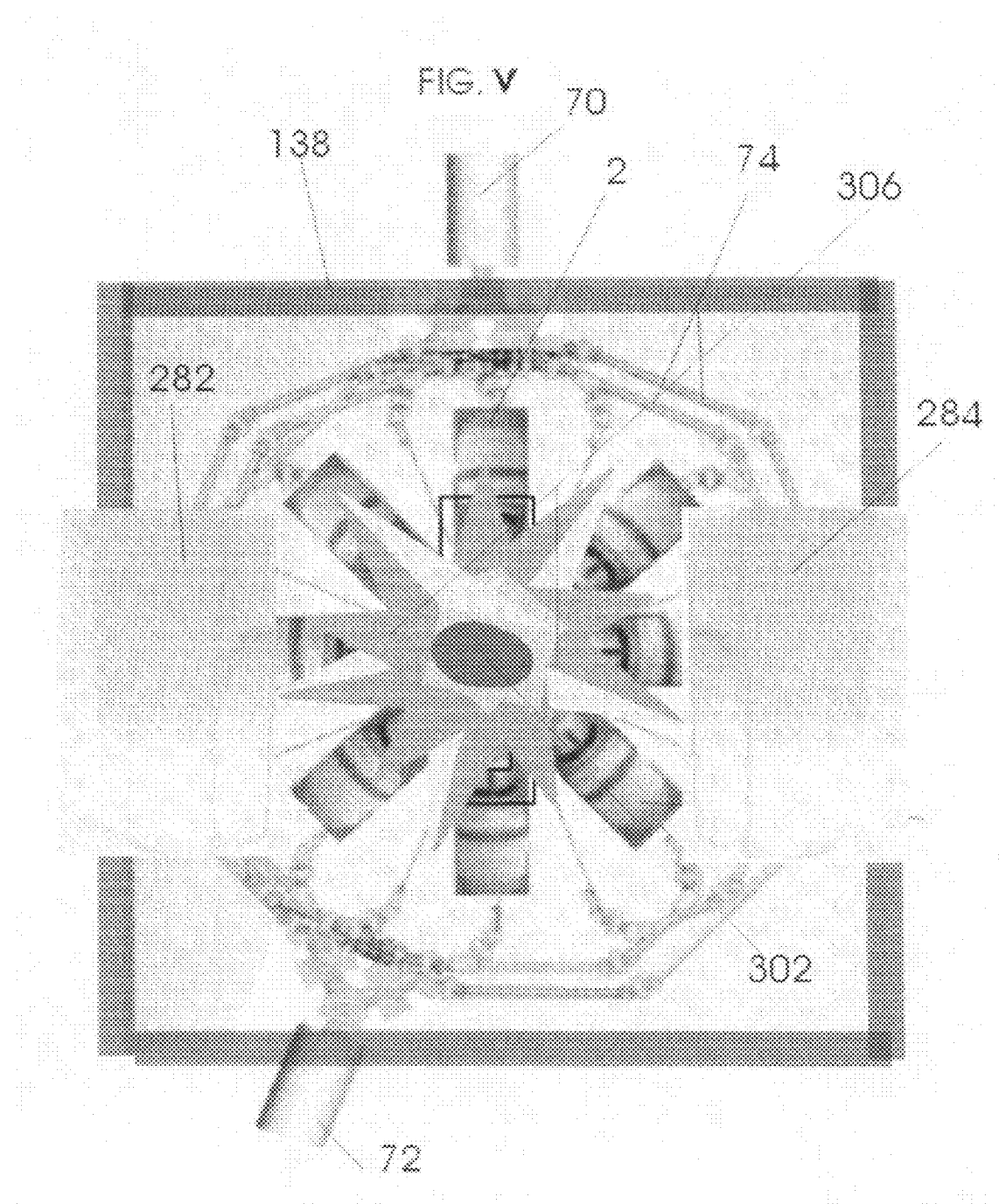

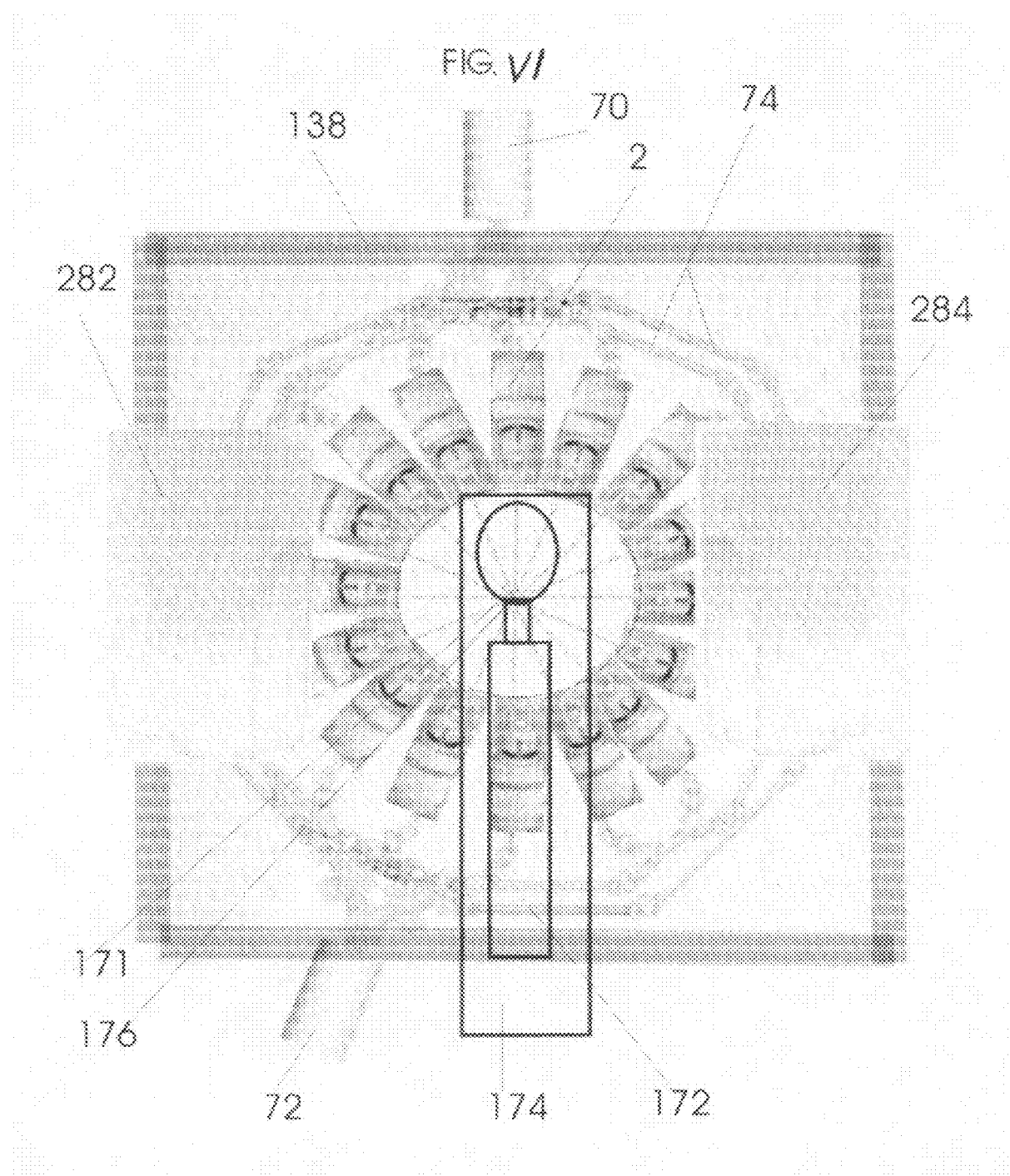

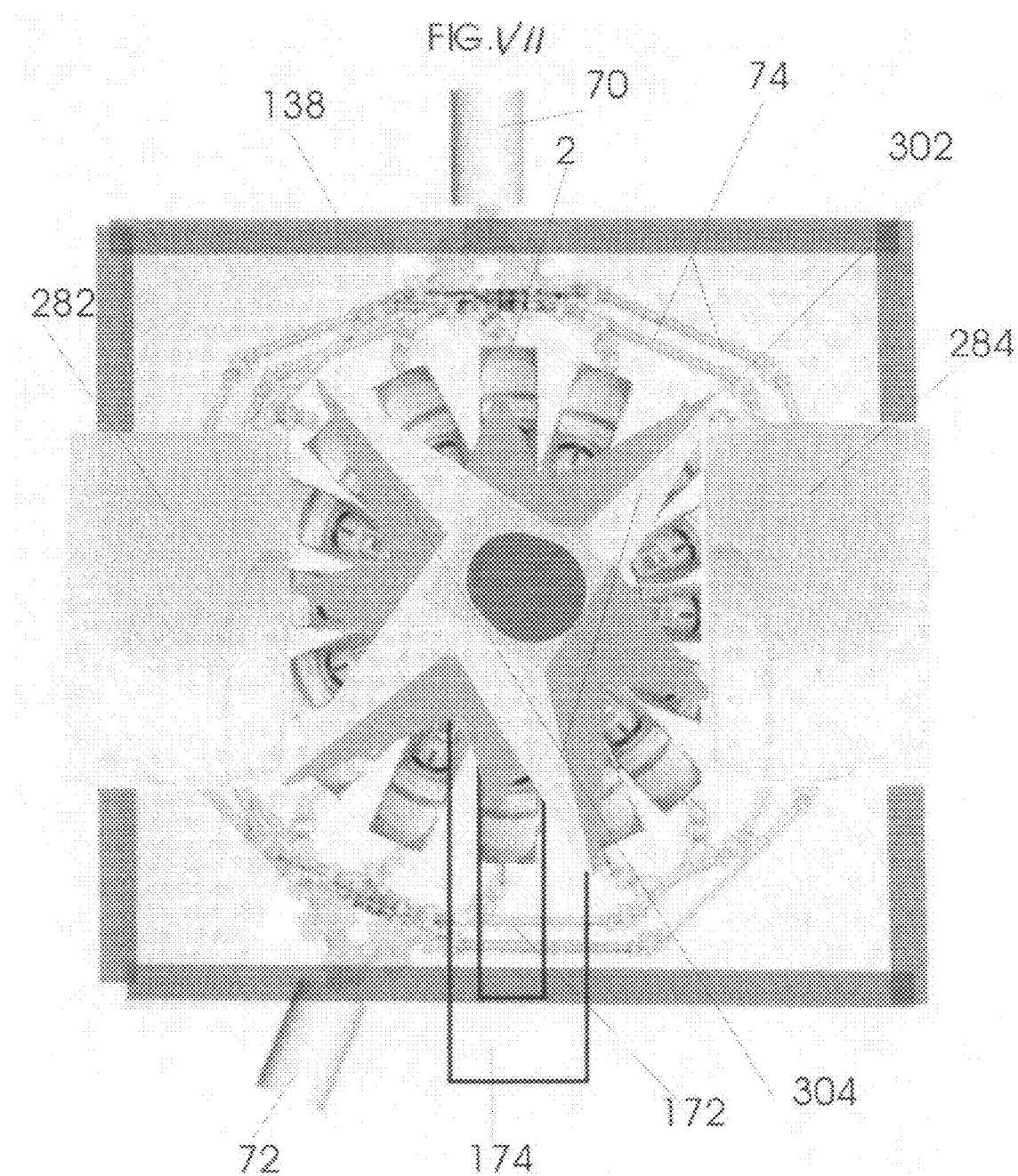

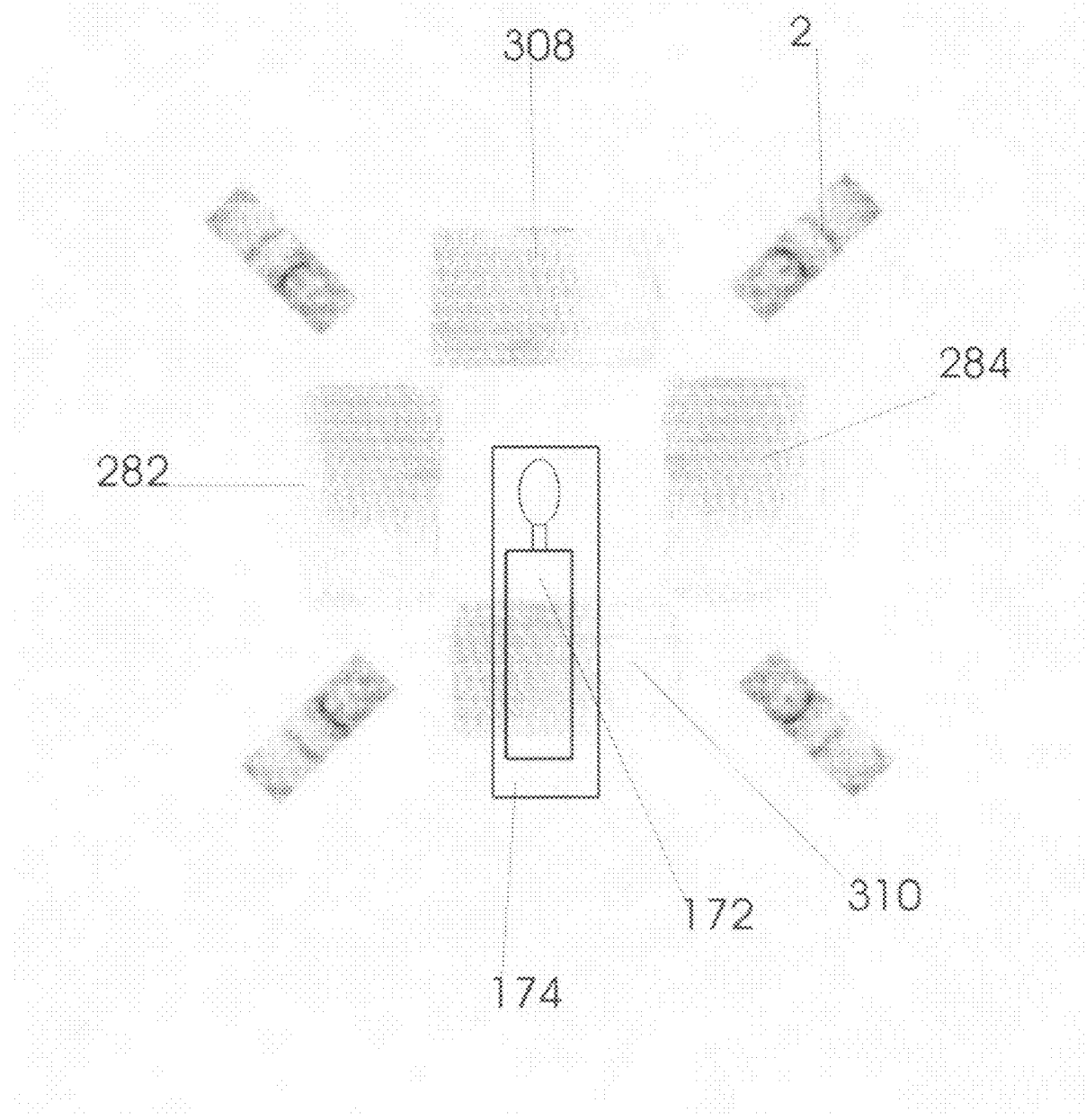

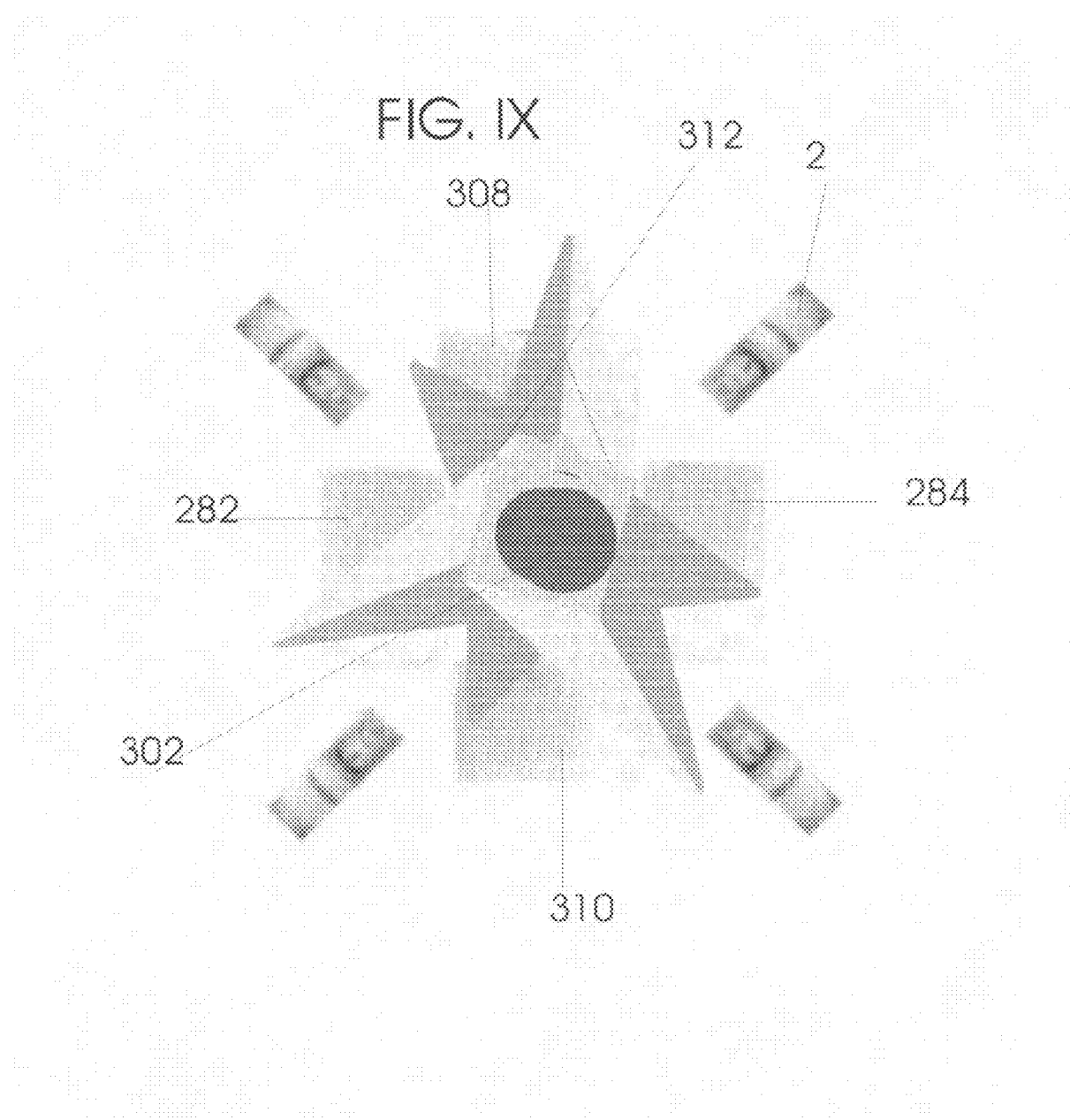

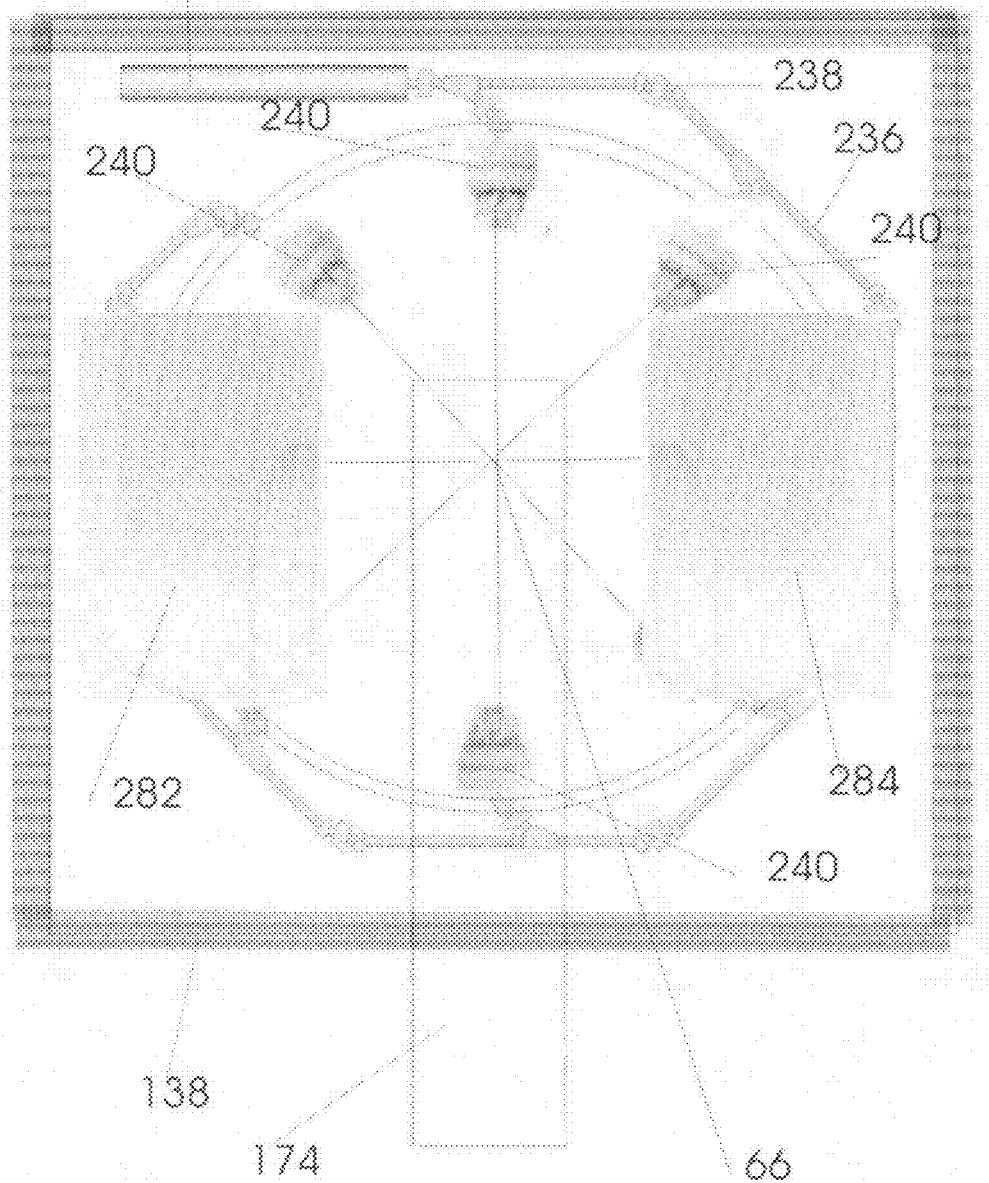

SINGLE SESSION INTERACTIVE ULTRA-SHORT DURATION SUPER-HIGH BIOLOGICAL DOSE RATE RADIATION THERAPY AND RADIOSURGERY

CROSS REFERENCE TO RELATED APPLICATIONS

This Application claims the benefit of U.S. provisional patent application, 60/790,192, filed on Apr. 6, 2006 and its regular patent application Ser. No. 11/784,398 filed on Apr. 5, 2007, its continuation application Ser. No. 11/974,876 filed on Oct. 15, 2007, Provisional Patent Application 60/872,117 filed on Nov. 30, 2006, its regular utility patent application Ser. No. 11/998,063 filed on Nov. 27, 2007, Provisional Patent Application 60/872,115, filed on Nov. 30, 2006, its regular utility patent Ser. No. 11/998,064 filed on Nov. 27, 2007, Provisional Patent Application 60/927,622 filed on May 3, 2007.

FIELD OF INVENTION

This invention relates to image guided radiation therapy with multiple radiating beams and treatment of all the treatment fields simultaneously or sequentially within a few seconds to improve tumor cure and control and to minimize the radiation associated toxic effects to normal tissue.

1. BACKGROUND OF THE INVENTION

The advantages of image guided all field synchronous radiation therapy is described in U.S. Provisional Patent Application No. 60/790,192 filed on Apr. 6, 2006, its regular Utility patent application Ser. No. 11/784,398 Filed on Apr. 5, 2007, its continuation application Ser. No. 11/974,876 filed on Oct. 15, 2007 "Multiple Medical Accelerators and kV-CT Incorporated Radiation Therapy Device and Semi-Automated Custom Reshapeable Blocks for All Field Synchronous Image Guided 3-D Conformal-Intensity Modulated Radiation Therapy", Provisional Patent Application 60/872,117 of Nov. 30, 2006, its regular Utility patent application Ser. No. 11/998,063, filed on Nov. 27, 2007 "Lethal and Sublethal Damage Repair Inhibiting Image Guided Simultaneous All Field Divergent and Pencil Beam Photon and Electron Radiation Therapy and Radiosurgery", Provisional Patent Application 60/872,115 of Nov. 30, 2006, its regular utility patent application Ser. No. 11/998,064 filed on Nov. 27, 2007, "Lethal and Sublethal Damage Repair Inhibiting Image Guided Split Dose, Few Seconds Interval Divergent and Pencil Photon and Electron Radiation Beams Radiation Therapy and Radiosurgery", Provisional Patent Application 60/927,622 filed on May 3, 2007, "Single Session Interactive Image Guided Simulation, Field Shaping, Treatment Planning and Ultra Short Duration Super-High Biological Dose Rate All Field Simultaneous or Sequential Radiation Therapy and Radiosurgery" and their related Disclosure Document 561105 filed on Sep. 14, 2004.

The methods of kV CT and MV-CT are described in the above cross-referenced applications. They are modified and adapted in this invention's online dynamic interactive viewing of the surface and internal anatomy as 3-D and 4-D VR CT or 3-D and 4-D VR MRI images and treatment planning. When the Medical Accelerator System is combined with CT imaging only, the CT imaging is used for interactive single session combined simulation, block making and treatment planning and radiation therapy. When the Medical Accelerator System is equipped with both CT and MRI imaging capabilities, CT and MRI imaging is used for interactive single session combined simulation, block making, treatment planning and radiation therapy. CT-MRI fused images are used for the treatment planning. It overcomes the difficulties associated with MRI's non-correlating pixel intensities between bone-air interface as with MRI of the sinuses. It also eliminates the need to introduce an endorectal probe for MRI of the prostate. The fused CT-MRI image provides sufficient imaging details of the prostate for the treatment planning.

The MRI also facilitates to do the functional imaging by magnetic resonance spectroscopic imaging (MRSI). The CT combined with MRI and functional imaging the MRSI are also used for online dynamic interactive views of the surface and internal anatomy of the treating tumor volume. The tumor volume is visualized as 3-D and 4-D VR images on a stereoscopic screen and as 2-D images on a 2-D monitor. It has greater significance in radiation therapy of cancer. It helps to improve precise simulation, block making and treatment planning and to improve the quality of radiation therapy.

The Medical Accelerator systems described in Provisional Patent Application 60/872,117 of Nov. 30, 2006, Lethal and Sublethal Damage Repair Inhibiting Image Guided Simultaneous All Field Divergent and Pencil Beam Photon and Electron Radiation Therapy and Radiosurgery facilitates actual beam on time to complete radiation therapy to all the setup fields in about 5 seconds and radiosurgery in about 30 seconds. Since a patient can hold breathing for more than 40 seconds, the breathing associated organ movement is not a hindrance to deliver accurate radiation therapy with the Medical Accelerator System describe in the above Provisional Patent Application 60/872,117. It simplifies the single session radiation therapy and radiosurgery to a patient with more precision and with limited patient fixation to the treatment table. It improves the patient's comfort significantly.

The single session simulation, block making, treatment planning and radiation therapy eliminates the protracted six to seven week long multiple session radiation therapy. In multiple session radiation therapy, reproduction of the same treatment setup for the daily treatment is an almost impossible task. Hence the single session treatment as described here further enhances the quality of the treatment.

Single Session All Field Simultaneous Radiation Therapy's Effective Dose Rate Equivalence to I-125 Implant, Conventional Radiation Therapy and IMRT and the Effective Dose Rate of Radiosurgery with Gamma Knife by Multiple Isocenters Total Dose and Dose Rate in I-125 Brachytherapy Brachytherapy with radioactive seeds has similarities to All Field Simultaneous Radiation Therapy (AFSRT) with multiple accelerators. In both radiation is rendered from multiple sources of radiation. Brachytherapy is a long duration radiation therapy with many radioactive seeds implanted into a single field made of multiple smaller fields in which the radiation from the implanted multiple radioactive seed's fuse together to give the implant volume radiation and the dose rate. If 20,736 cGy total dose is given by I-125 implant, its initial dose rate is 10 cGy/h. It is derived from the formula: Total dose=initial dose rate×$T_{ave}$. $T_{ave}$ is the mean life. The $T_{ave}$ of I-125 is 1.44×$T_{1/2}$=1.44×60 days=2073.6 hr; the $T_{1/2}$ for I-125=60 days. Hence the initial dose rate is 20,736/2,076.6=10 cGy/h. It is 0.1667 cGy/min or 0.0028 cGy/sec.

Effective Dose Rate in Conventional Radiation Therapy and IMRT when Machine Dose Rate is 400 cGy/min In conventional IMRT and radiosurgery, with radiation from multiple external beams, each fields of a multiple treatment setup is treated with a radiation beam. Each of those fields is treated as one field at a time. In this instance, the daily radiation therapy is rendered as sub-fractionated radiation. The cumulative dose of about 8,000 cGy of the conventional IMRT is rendered as fractionated daily dose of about 200 cGy and as five treatments in a week and no treatments on weekends. It lasts eight weeks of treatment or an overall treatment time of 56 days or 56×24 hours, that is in 1,344 hours. Since 8,000 cGy is given in an overall elapsed time of 1,344 hours, its overall dose rate is 5.9524 cGy/h or say, 6 cGy/h. It is 0.0992 cGy/min or say, 0.1 cGy/min which is 0.0017 cGy/sec.

Effective Dose Rate in AFSRT Versus Conventional IMRT when Machine Dose Rate is 400 cGy/min In AFSRT radiation to all the fields is rendered simultaneously with multiple external beams, each beams coming from each of the multiple accelerators containing radiation therapy machine. All the beams from a multiple field setup treatment converge together at the tumor site in a patient. At 400 cGy/min machine dose rate, it renders 200-cGy to the tumor in 5 seconds. Hence, its dose rate is 40 cGy per second. Compared to the above conventional IMRT's 0.0017 cGy/sec, this 40-cGy/sec-dose rate of AFSRT is 40/0.0017, which is 23,529. It is 23,529 times higher than the conventional IMRT's dose rate of 0.0017 cGy.

Effective Dose Rate in AFSRT Versus Conventional Radiosurgery with Multiple Isocenters as in Radiosurgery with Gamma Knife In AFSRT, 200 cGy could be delivered to a tumor in 5 seconds. Hence its dose rate is 40 cGy/sec.

The time taken to deliver 1,000 cGy to a tumor by radiosurgery with Gamma Knife and by multiple isocenters is about 3 hours (9). It is 333.33 cGy/h, 5.55 cGy/min and 0.0926 cGy/sec Since in the above example conventional radiosurgery rendered in 3 hours its dose rate is 0.0926 cGy/sec. The comparative dose rate for AFSRT-radiosurgery is 0/0.0926=432 times higher.

2. BRIEF DESCRIPTION OF THE DRAWINGS

FIG. I is an illustration of 6 accelerators configured with an open magnet for combined MV-CT and MRI image guided radiation therapy and radiosurgery with six transverse plane coplanar beams.

FIG. IIA shows non-coplanar beams from accelerator treatment heads that are arranged circularly around the imaging and treatment table to render non-coplanar beams and the open magnet for image guided all fields' simultaneous radiation therapy and radiosurgery.

FIG. IIB illustrate accelerator treatment heads arranged in coplanar and non-coplanar planes that includes the transverse, lateral-sagital and cranio-caudal-coronal closed circular gantries and the open magnet for image guided all fields' simultaneous radiation therapy and radiosurgery FIG. IIC shows accelerator treatment heads arranged in coplanar and non-coplanar gantries that includes transverse, lateral-sagital and cranio-caudal-coronal half-circular gantries and the open magnet's segments as inserted in between the half-circular gantries for image guided all fields' simultaneous radiation therapy and radiosurgery FIG. II shows eight non-coplanar beams converging onto the tumor.

FIG. III—illustrates coplanar beams from transversely placed accelerators and non-planar beams from accelerators in non-transverse planes and the open magnet for MRI FIG. IV is an illustration of two four-beam accelerators connected with two octagonal beam lines and eight treatment heads and an open magnet for MV-CT and MRI image guided simultaneous radiation therapy and radiosurgery with up to 8 transverse plane beams FIG. V is an illustration of two four-beam accelerators connected with two octagonal beam lines and eight treatment heads eight transverse plane beams and ten non-coplanar beams and an open magnet for MV-CT and MRI image guided simultaneous radiation therapy and radiosurgery with up to 8 transverse plane beams and up to 10 non-coplanar beams.

FIG. VI is an illustration of two four-beam accelerators connected with two octagonal beam lines and 16 treatment heads and an open magnet for MV-CT and MRI image guided simultaneous radiation therapy and radiosurgery with up to 16 transverse plane beams FIG. VII is an illustration of two four-beam accelerators connected with two octagonal beam lines and sixteen treatment heads sixteen transverse plane beams and eight non-coplanar beams and an open magnet for MV-CT and MRI image guided simultaneous radiation therapy and radiosurgery with up to sixteen transverse plane beams and up to eight non-coplanar beams.

FIG. VIII is an illustration of 4 accelerators configured with two open magnets for combined MV-CT, MRI and MRSI-image guided radiation therapy and radiosurgery with four transverse plane coplanar beams.

FIG. IX is an illustration of 4 accelerators in transverse plane and 6 non-coplanar accelerators configured with two open magnets for MV-CT, MRI and MRSI-image guided simultaneous radiation therapy and radiosurgery with up to 4 transverse plane beams and up to 6 non-coplanar beams.

FIG. X shows one single beam accelerating waveguide connected with an octagonal beam line to steer the electron beams from the waveguide to eight targets in eight treatment heads arranged in a circular gantry as pairs opposing each other and with superimposed open magnet for image guided sequential treatment of each fields at few second intervals.

3. REFERENCE NUMERALS

2 Treatment head
4 Collimation and accessory holder
66 Isocenter
70 Four beam accelerator-1
72 Four beam accelerator-2
74 Top and bottom beam lines
75 Left top and bottom beam lines for left top and bottom beams
138 Lead vault shielding
171 Isocenter
172 Patient
174 Imaging and treatment table
176 Converging isocentric beams on patient's tumor site
234 Single beam accelerator
236 Octagonal beam line
238 Bending and focusing magnets for octagonal beam bend
240 Treatment head connected with beam-line
282 Open magnet segment one
284 Open magnet segment two
286 Non-coplanar beam from 0°
288 Non-coplanar beam from 45°
290 Non-coplanar beam from 90°
292 Non-coplanar beam from 135°
294 Non-coplanar beam from 180°
296 Non-coplanar beam from 225°
298 Non-coplanar beam from 255°
300 Non-coplanar beam from 315°

302 Tumor
304 Combined 8 non-coplanar beams focused towards the tumor
306 Combined 10 non-coplanar beams focused towards the tumor
308 Cranial open magnet segment one
310 Caudal open magnet segment two
312 Combined 6 non-coplanar beams focused towards the tumor
314 Accelerator in non-coplanar plane
316 Converging non-coplanar 7 beams
318 Circular planes
320 Accelerator in coplanar plane
322 Coplanar AP accelerator
324 Coplanar PA accelerator
326 Circular transverse plane gantry
338 Circular lateral-sagital-plane gantry
330 Circular coronal-circular plane gantry

4. DESCRIPTION OF THE PREFERRED EMBODIMENTS

FIG. I is an illustration of 6 accelerators configured with an open magnet for combined MV-CT and MRI image guided radiation therapy and radiosurgery with six transverse plane coplanar beams. The accelerators 2 are configured at 0.45, 135, 180, 225 315 degree angles. An open magnet's two segments are placed in between the table on which the patient is placed during imaging. The open segment one 282 and the open magnet segment two 284 placed in between is a conventional open magnet MRI but adapted to work together with the medical accelerator and configured as to fit with the accelerator arrangements. The accelerator and the segments of the magnet are in a transverse plane. Both MV-CT and MRI combined imaging are used for image guided radiation therapy and radiosurgery. With a strong magnet and its strong magnetic field the functional imaging by magnetic resonance spectroscopic imaging, MRSI is also made feasible. The shielding is made of non-magnetic material. In this instance, it is made of lead. The lead vault shielding 138 surrounds the accelerator and the magnet. The patient-table is also made of non-magnetic material. The patient on imaging and treatment table 172 is positioned for the treatment.

FIG. IIA shows non-coplanar beams from accelerator treatment heads that are arranged circularly around the imaging and treatment table to render non-coplanar beams and the open magnet for image guided all fields' simultaneous radiation therapy and radiosurgery. The converging non-coplanar beams 316 is shown as focused onto the tumor 302. The imaging and treatment table 174 is inserted at the center of thus configured radiation therapy machine. The open magnet segment-1, 282 is placed superiority and the open magnet segment-2, 284 is placed as inferiority to the imaging and treatment table. The circular planes 318 illustrate the position of the accelerator heads around the imaging and treatment table 174. Both MV-CT and MRI combined imaging are used for image guided radiation therapy and radiosurgery. With a strong magnet and its strong magnetic field the functional imaging by magnetic resonance spectroscopic imaging, MRSI is also made feasible.

FIG. IIB illustrate accelerator treatment heads arranged in coplanar and non-coplanar planes that includes the transverse, lateral-sagital and cranio-caudal-coronal closed circular gantries and the open magnet for image guided all fields' simultaneous radiation therapy and radiosurgery. The accelerators of coplanar plane 320 are arranged in a circular transverse plane gantry 326 and the accelerators in non-coplanar plane 314 are placed in circular coronal plane gantry 330. Additional non-coplanar accelerators could be arranged in circular lateral-sagittal plane gantry 328. The coplanar AP accelerator 322 and the coplanar PA accelerator 324 renders the anterior-posterior (AP) and the posterior-anterior (PA) beams directed towards the imaging and treatment table 174. The open magnet segment one, 282 and the open magnet segment two, 284 are placed laterally and as opposing to each other. Both MV-CT and MRI combined imaging are used for image guided radiation therapy and radiosurgery. With a strong magnet and its strong magnetic field the functional imaging by magnetic resonance spectroscopic imaging, MRSI is also made feasible. The gantries are fixed and non-rotating but the treatment heads are equipped with scanning beams to obtain few degree gantry rotational effect and beam's intensity modulation.

FIG. IIC shows accelerator treatment heads arranged in coplanar and non-coplanar gantries that includes transverse, lateral-sagital and cranio-caudal-coronal half-circular gantries and the open magnet's segments as inserted in between the half-circular gantries for image guided all fields' simultaneous radiation therapy and radiosurgery. The accelerators in coplanar plane 320 are arranged in cut circular transverse plane gantry 332 and the accelerators in non-coplanar plane 314 are placed in cut circular coronal plane gantry 334. Additional non-coplanar accelerators could be arranged in circular lateral-sagittal plane gantry 328. The coplanar AP accelerator 322 and the coplanar PA accelerator 324 renders the AP PA beams that are directed towards the imaging and treatment table 174. The open magnet segment one 282 and the open magnet segment two 284 are placed laterally and as opposing to each other. It renders additional working space in between open magnet multiple plane gantries 336. Both MV-CT and MRI combined imaging are used for image guided radiation therapy and radiosurgery. With a strong magnet and its strong magnetic field, functional imaging by magnetic resonance spectroscopic imaging, MRSI is also made feasible. The gantries are fixed and non-rotating but the treatment heads are equipped with scanning beams to obtain few degree gantry rotational effect and beam's intensity modulation.

FIG. II shows eight non-coplanar beams converging onto the tumor. Along with the coplanar beams from the transverse plane, these non-coplanar beams from coronal and lateral-sagittal planes converge onto the tumor 302. The accelerators are placed in such a manner as to facilitate the beam's directions towards the tumor. Eight non-coplanar beams are shown as converging on to the tumor 302. They include non-coplanar beams from 0 degree, 386, from 45 degree, 288, from 90 degree, 290, from 135 degree, 292, from 180 degree, 294, from 255 degree, 298 and from 300 degree, 315 degree. The number of such non-coplanar beams could be increased or decreased based upon the clinical need of such multiple beams for simultaneous radiation therapy to all the treatment fields. The fused MRI and the MV-CT images are used to generate the VR 3-D image rendering for single session image guided radiation therapy planning, field shaping block making and radiation therapy and radiosurgery.

FIG. III—illustrates coplanar beams from transversely placed accelerators and non-planar beams from accelerators in non-transverse planes. In this case, the six coplanar beams shown in FIG. I is combined with eight non-coplanar beams shown in FIG. II. Each of the six accelerators 2 placed in transverse planes at varying angles provides coplanar beams. The eight non-coplanar beams 304 from lateral and coronal planes and the six coplanar beams from the transverse plane all converge on to the tumor 302 for simultaneous all field radiation therapy and radiosurgery. The open magnet section one 282 and the open magnet segment two 284 are the cut sections of the magnet for the MRI. Both MV-CT and MRI combined imaging are used for image guided radiation therapy and radiosurgery. With a strong magnet and its strong magnetic field the functional imaging by magnetic resonance spectroscopic imaging, MRSI is also made feasible. The fused MRI and the MV-CT images are used to generate the VR 3-D image rendering for single session image guided radiation therapy planning, field shaping block making and radiation therapy and radiosurgery.

FIG. IV is an illustration of two four-beam accelerators connected with two octagonal beam lines in transverse plane and eight coplanar treatment heads and an open magnet for MV-CT and MRI image guided simultaneous radiation therapy and radiosurgery with up to 8 transverse plane beams. The four beam accelerators combined with the octagonal beam lines are described in Provisional Patent Applications 60/872,117 and 60/872,115. The accelerator 70 and the accelerator 72 are connected to the top and bottom beam lines 74. The treatment heads 2 are arranged as opposing to each other and at intervals of 45-degree angles, with eight treatment heads. The entire system is enclosed within non-magnetic lead shield vault 138. Other high density non-magnetic shielding could also be used for the shielding. The open magnet segment one 282 and the open magnet segment two 284 are placed laterally and as opposing to each other. The patient 172 is shown as laying on the imaging and treatment table 174. Additional accelerators and the transverse plane beam lines and coplanar treatment heads could be arranged in other planes like in lateral-sagital and cranio-caudal-coronal planes. Both MV-CT and MRI combined imaging are used for image guided radiation therapy and radiosurgery. With a strong magnet and its strong magnetic field, functional imaging by magnetic resonance spectroscopic imaging, MRSI is also made feasible.

FIG. V is an illustration of two four-beam accelerators connected with two octagonal beam lines and eight treatment heads eight transverse plane beams and ten non-coplanar beams and an open magnet for MV-CT and MRI image guided simultaneous radiation therapy and radiosurgery with up to 8 transverse plane beams and up to 10 non-coplanar beams. Like in FIG. IV, the accelerator 70 and the accelerator 72 are connected to the top and bottom beam lines 74. The transverse plane treatment heads 2 are arranged as opposing to each other and at intervals of 45-degree angles, thus with eight treatment heads. In addition, beams from treatment heads arranged in lateral-sagital and cranio-caudal-coronal planes are also shown. Combined 10 non-coplanar beams focused towards the tumor 306 is shown as superimposed on to the transverse plane beams. The entire system is enclosed within non-magnetic lead shield vault 138. Other high density non-magnetic shielding could also be used for the shielding. The open magnet segment one 282 and the open magnet segment two 284 are placed laterally and as opposing to each other. Both MV-CT and MRI combined imaging are used for image guided radiation therapy and radiosurgery. With a strong magnet and its strong magnetic field, functional imaging by magnetic resonance spectroscopic imaging, MRSI is also made feasible.

FIG. VI is an illustration of two four-beam accelerators connected with two octagonal beam lines and 16 treatment heads and an open magnet for MV-CT and MRI image guided simultaneous radiation therapy and radiosurgery with up to 16 transverse plane beams. The accelerator 70 and the accelerator 72 are connected to the top and bottom beam lines 74. The treatment heads 2 are arranged as opposing to each other and at intervals of 22.5-degree angles, with 16 treatment heads. The entire system is enclosed within non-magnetic lead shield vault 138. Other high density non-magnetic shielding could also be used for the shielding. The open magnet segment one 282 and the open magnet segment two 284 are placed laterally and as opposing to each other. The patient 172 is shown as laying on the imaging and treatment table 174. Additional accelerators and the transverse plane beam lines and coplanar treatment heads could be arranged in other planes like in lateral-sagital and cranio-caudal-coronal planes. Both MV-CT and MRI combined imaging are used for image guided radiation therapy and radiosurgery. With a strong magnet and its strong magnetic field, functional imaging by magnetic resonance spectroscopic imaging, MRSI is also made feasible. Additional accelerators and the transverse plane beam lines and coplanar treatment heads could be arranged in other planes like in lateral-sagital and cranio-caudal-coronal planes.

FIG. VII is an illustration of two four-beam accelerators connected with two octagonal beam lines and sixteen treatment heads sixteen transverse plane beams and eight non-coplanar beams and an open magnet for MV-CT and MRI image guided simultaneous radiation therapy and radiosurgery with up to sixteen transverse plane beams and up to eight non-coplanar beams. The accelerator 70 and the accelerator 72 are connected to the top and bottom beam lines 74. The transverse plane treatment heads 2 are arranged as opposing to each other and at intervals of 22.5-degree angles, thus with 16 treatment heads. In addition, beams from treatment heads arranged in lateral-sagital and cranio-caudal-coronal planes are also shown. Combined 8 non-coplanar beams focused towards the tumor 306 is shown as superimposed on to the transverse plane beams. The entire system is enclosed within non-magnetic lead shield vault 138. Other high density non-magnetic shielding could also be used for the shielding. The open magnet segment one 282 and the open magnet segment two 284 are placed laterally and as opposing to each other. Both MV-CT and MRI combined imaging are used for image guided radiation therapy and radiosurgery. With a strong magnet and its strong magnetic field, functional imaging by magnetic resonance spectroscopic imaging, MRSI is also made feasible.

FIG. VIII is an illustration of 4 accelerators configured with two open magnets for combined MV-CT, MRI and MRSI-image guided radiation therapy and radiosurgery with four transverse plane coplanar beams. The two open magnet combination facilitates a stronger magnetic field for functional imaging by magnetic resonance spectroscopic imaging, MRSI. Four treatment heads 2 are arranged in transverse plane for coplanar treatment. I addition to the laterally placed open magnet segment one 282 and open magnet segment 284, two other magnet segments, the cranial open magnet segment 308 and caudal open magnet 310 are also shown. The open magnet segment one 282 and the open magnet segment two 284 forms the first open magnet and the cranial open magnet segment 308 and the caudal open magnet 310 forms the second open magnet. The patient 172 is shown as laying on the imaging and treatment table 174. Both MV-CT and MRI combined imaging are used for image guided radiation therapy and radiosurgery. With the combined two open magnets and their stronger magnetic field, the functional magnetic resonance spectroscopic imaging, MRSI is made easier.

FIG. IX is an illustration of 4 accelerators in transverse plane and 6 non-coplanar accelerators configured with two open magnets for MV-CT, MRI and MRSI-image guided simultaneous radiation therapy and radiosurgery with up to 4 transverse plane beams and up to 6 non-coplanar beams. Combined 6 non-coplanar beams focused towards the tumor 312 is shown as superimposed on to the 4 transverse plane beams from four transverse plane accelerators. The two open magnet combination facilitates a stronger magnetic field for functional imaging by magnetic resonance spectroscopic imaging, MRSI. Four treatment heads 2 are arranged in transverse plane for coplanar treatment. I addition to the laterally placed open magnet segment one 282 and open magnet segment 284, two other magnet segments, the cranial open magnet segment 308 and caudal open magnet 310 are also shown. The open magnet segment one 282 and the open magnet segment two 284 forms the first open magnet and the cranial open magnet segment 308 and the caudal open magnet 310 forms the second open magnet. The patient 172 is shown as laying on the imaging and treatment table 174. Both MV-CT and MRI combined imaging are used for image guided radiation therapy and radiosurgery. With the combined two open magnets and their stronger magnetic field, the functional magnetic resonance spectroscopic imaging, MRSI is made easier.

FIG. X shows one single beam accelerating waveguide connected with an octagonal beam line to steer the electron beams from the waveguide to eight targets in eight treatment heads arranged in a circular gantry as pairs opposing each other and with superimposed open magnet segments. It is used for sequential treatment at few second intervals. The accelerator waveguide 234 is placed at 0° and is connected with an octagonal beam line 236. The bending and focusing magnets 238 steers the electron beam through the beam line at each bends of the octagonal beam line 236. The treatment heads 240 are arranged in transverse plane. The beams from the treatment are focused at the isocenter 66 that is shown on the imaging and treatment table 174. The open magnet segment one 282 is and open magnet segments two are placed laterally at 90 and 270 degrees. In this illustration, some of the treatment heads are hidden by the open magnet segments one 282 and open magnet segment two. Additional beam bending and steering magnets are used to arrange the treatment heads so that the path of its beam is not interfered by the segments of the magnet. It is not a rotating machine. The accelerator, the beam lines, the treatment heads and the open magnet are all placed within a heavy metal shield, 138. This form of shielding reduces shielding requirement for the treatment head and thus the weight of the treatment heads. Such radiation shielding non-magnetic suitable metals for this machine includes lead, tungsten, Cerrobend or steel

5. METHODS OF OPERATION

The individually fitting body frame with cut windows representing each of the multiple treatment fields or inflatable air bags with clamped non-inflatable windows representing the treatment fields and in which a patient can be fitted is used to fix the patient to the imaging-treatment table. The inflatable air bag is fitted on the imaging and treatment table 174. With such airbags, it takes only a few minutes to fix the patient in desired position for the treatment. The treatment itself lasts only a few seconds during which an ambulatory patient with no respiratory discomfort can hold the breath very easily. If the body frame is used, it is made of non-magnetic materials. The patient is fitted into this body frame tightly. The body frame is made as those described by Strassmann et al for single session extracranial radiation therapy (7) but without any MRI interfering objects attached to it if the Medical Accelerator System has both CT and MRI imaging capabilities and with cut windows for beam entrance to spare the skin from radiation.

When ready to acquire live CT and MRI video of the treatment region, patient is instructed to hold breath to 30 to 50 seconds during which a series of CT or MRI scans are taken. If the patient has to breathe before the completion of the MRI scan series, patient is instructed to breath and the MRI scanning is interrupted while the patient is breathing. When the patient is comfortable patient is instructed to breathing again and the CT and MRI imaging is continued. These images are reconstructed by the image-processing computer and projected onto a 3-D stereoscopic LCD monitor as 3-D VR CT or MR images and onto a 2-D monitor as 2-D CT or MR images. It also includes the scout views of the patient's treatment area. By the click of a computer-mouse desired images are projected onto these screens.

Multiple beams are used to render the treatment to all the treatment fields simultaneously. Their field sizes vary. Each beam is collimated with primary and secondary collimators. Multiple smaller fields within a smaller field is treated like the "step and shoot" method of treatment with MLC. However there are no MLC in this case. Alternatively, individual treatment field is shaped with the field shaping tungsten powder mixture paste.

Each of the treatment head's accessory holders is equipped with a block-forming tray containing the beam blocking tungsten powder mixture that is made into a thick paste by mixing it with resin that acts like a binder. Methods of such tungsten powder block making are described in previous U.S. Provisional Patent Application 60/790,192, filed on Apr. 6, 2006 and its regular Patent Application filed on Apr. 5, 2007. It is adapted to make tungsten powder blocks in this instance. Tungsten is non-magnetic and hence it does not to interfere with magnetic field environment in which such blocks are made. The height of the blocking material is calculated as in usual field shaping blocks that blocks over 98 percent of the entering high energy radiating beam and allows only about less than 2 percent of the beam to pass through it. Such beam blocking trays are made with varying sizes of central and lateral open spaces. By pushing the paste like blocking material towards the central opening, that is towards the center of the beam or towards the lateral open space, that is away from the central opening, the treatment fields are shaped in conformity with the treatment field. The light field from the treatment head passes through the block on the accessory holder. The treatment heads, the accessory holders, the block forming trays are all placed away from the patient.

To make the field shaping blocks, the CT or the MRI scout image is projected as 3-D VR image onto the stereoscopic and 2-D monitors. If the system has only CT imaging capability, the CT scout image is used in the block making process. If the system has both CT and MRI imaging capability, based upon the anatomical site's clarity for block making, the CT or the MRI scout image is used in the block making process. The light from the treatment head passing through the block on the block-forming tray simulates the beam eye view of the radiating beam. It is projected as the beam coming from a treatment field and falling on to the 3-D VR CT or the MR image on the stereoscopic screen. It is also projected onto the 2-D monitor.

Pliable block making tungsten powder mixture is inserted into a block-making container and this container is placed on to the accessory holder. It is aligned with the light field like the placement of a field-shaping block on to the accessory holder. The 3-D VR image of the patient's scout view with the tumor is projected on the stereotactic monitor and 2-D view monitor. With the aid of the computer menus that helps to shape the field the beam shaping block's opening is shaped in conformity with each treatment fields. Working with adjustable block forming material on the block-forming tray, the opening of the block is shaped and adjusted to encompass the tumor volume with one-cm margin as described above.

The tungsten powder mixture is pushed forward or backward to increase or decrease the size of the block's opening. For the final adjustment, half a cm per half a cm blocking material is pasted or removed with a long half a-cm width sized spatula. If the field opening is to be decreased, additional blocking material is added at the desired regions within the open area of the beam block. In this case, each 0.3 to 1-cm width blocking material is added with the aid of a blocking material injector. This injector is made to extrude selectable volume of the blocking material ranging from 3 mm to a cm width at a time. Based upon the energy sleeted, the thickness along the primary beam direction is adjusted to allow only less than 2 percent of the primary beam transmission. Shielding the areas that is outside of the block opening with the jaws further reduces the primary beam transmission through this block. Since this block is made as in continuity without any interruptions in between the paste like blocking material, there is no interleaf transmission of the primary beam as it is with MLC. Adding or decreasing the block opening, adjusting its height with the paste like blocking material with on-line computation of percent beam transmission and its tight smoothening with a spatula helps to make the block opening as in conformity with the tumor volume and its margins.

The interleaf transmission of the primary beam by MLC is about 3 percent of the primary beam. The Cerrobend block transmits about 3.5 percent of the primary beam. The image and online computer calculations of the percent beam transmission aided blocks thus made transmits less primary beam through the blocked regions than the primary beam transmission by the MLC and the Cerrobend blocks. Multiple beams from varying angles are used for simultaneous treatment of all the treatment fields. Each of the treatment fields is similarly simulated and its shaped field block is made to make the beam to pass through the opening in the block in conformity with the geometry of the tumor region treated from that field.

At the end of all field shaping, the light fields from all the shaped fields are projected together onto the 3-D and or 4-D VR MR-image on the stereoscopic monitor and to the 2-D monitor to check the combined treatment beam's conformity with the 3-D and or 4-D tumor volume. If any one of the beams coming from the shaped field is not in conformity with the 3-D or 4-D VR tumor volume and its margin, then it is adjusted by increasing or decreasing the block opening as described above.

Thus the radiation oncologist works like a surgeon and a sculptor to shape each of the treatment field's blocks that fits with the tumor volume and its margins so that it fits tightly like a tailor-made attire to do the tight fitting radiosurgery. Such tight fitting radiosurgery helps to eliminate the tumor volume and its margins more efficiently than by the surgical resection of a tumor. By the surgical resection of a tumor, there are no certainty on the total removal of the tumor, especially of its microscopic remnants in the tumor bed and its spread towards its margins. Most often, surgery needs to be followed by radiation to treat the residual tumor and its microscopic spreads, hence the surgical resection is a two step treatment procedure. On the other hand, the radiosurgery is a single step treatment procedure. It preserves the functional integrity of an organ much better than surgery. The preservation of the functional integrity of the larynx or the tongue by radiation therapy is a classical example for the difference in functional preservation of an organ by radiation therapy and surgery.

After such block making, repeat CT and or MR-images are taken to check the conformal filed setup that encompasses the entire tumor volume with desired margins. Like before, those images are projected on to the stereotactic 3-D monitor and to 2-D monitor to check the field setups and the beams full coverage of the tumor. If it is found to be satisfactory and if it is a Medical Accelerator system with both CT and MRI, then the CT images are fused with the MRI. Such fused CT-MRI images are used for the treatment planning. If further adjustments in block's opening are needed, then the necessary such adjustments are made as describe above before proceeding to take the planning CT and MRI scanning.

The fused CT and MRI images are stored in the treatment-planning computer for 3-D conformal intensity modulated radiation therapy planning. The treatment planning is done by the Monte Carlo method of dose calculation in advanced computing system that can complete the treatment planning and calculations in about a minute. Such combined treatment planning and dose calculation further improves the quality of the treatment.

Like in the present image guided radiation therapy, the treatment-planning computer reconstructs the 2-D images to 3-D images and its segmentations for the treatment planning. Its 3-D VR format is used for treatment planning and dose calculations. Live interactive surface and internal anatomy of the treatment site is projected as 3D-VR-image format with superimposed isodose curves onto the stereoscopic monitor and as 3-D beam's eye view onto the 2-D monitor. Live interactive necessary adjustments are made to the beam's energy, dose rate and weights with the patient in treatment position and ready to be treated. The advanced treatment planning computing system calculates the dose distribution using the Monte Carlo methods of dose calculation in about a minute. Usually, the Monte Carlo method of dose calculations with an ordinary computer takes about 18 hours but it could be done within 10 hours by an Adjoint Monte Carlo method of treatment planning and dose calculation (8). For this single session, interactive simulation, block making treatment planning and treatment, fast 3-D Monte Carlo Method of treatment planning decreases the treatment planning time to about a minute. It is done with much improved computing system and by making necessary modifications to the Monte Carlo method of dose calculation. With the aid of a library of treatment plans for various sites and tumor and automatic optimization of such preplans to suite the treatment plan for the patient being treated such fast 3-D treatment planning is made possible.

A central fast treatment plan processing supercomputer to which the patient's treatment data is entered after the final processing of such radiation therapy setup is used for interactive TeleMedicine-radiation therapy and radiosurgery. With visualization of the 3-D VR images with the tumor volume on the stereotactic monitor and 2-D images on 2-D monitor at both distant centers, necessary final adjustments to the treatment plan are made interactively. Such interactive assistance for radiation therapy and radiosurgery between the two distant Radiation Oncology Centers facilitates advanced radiation therapy and radiosurgery at anywhere in the world.

Intensity Modulated Radiation Therapy to the Entire 3-D-4-D Tumor Volume and its Margins The intensity modulation of the beam for IMRT is done by selection of pencil or divergent beams and desired energy as described in the Provisional Patent Application 60/872,117 of Nov. 30, 2006, Lethal and Sublethal Damage Repair Inhibiting Image Guided Simultaneous All Field Divergent and Pencil Beam Photon and Electron Radiation Therapy and Radiosurgery. This Medical Accelerator System is equipped with multiple accelerators and multiple treatment heads that can deliver elementary beams of varying energy, beam weight and field sizes. The computer generated treatment plan calculates the energy, dose rate, field size and the beam weight for each of the beam from each of the accelerator. It is further modified with combined scanned elementary pencil beams from selected accelerators and divergent beams from other accelerators. Additional beam's intensity modulation is achieved by simple insertion of computer calculated width and thickness blocking material that can be easily formed to compensate the missing tissue, inhomogeneity and the curvature of the treatment field on the patient. From the CT and the MRI, the treatment-planning computer calculates it. However treating by the computer generated treatment plan calculated energy, dose rate, field size and the beam weight for each of the beam from each of the accelerator and treating all the treatment fields simultaneously provides better intensity modulated radiation to the entire 3-D tumor volume and its margins without the need for additional blocking materials insertion for the intensity modulated radiation therapy to the whole tumor.

It has some similarity with multisegmented static field radiation therapy with MLC. However in this instance there is no "stop and shoot" delivery methods of radiation though each field's treatment has likeness to the step and shoot method as described earlier. Furthermore, the radiation to the tumor is rendered with much lesser monitor units than when a tumor is treated by the IMRT with MLC. Hence there is much lesser scattered and leakage radiation and thereby much lesser radiation to the normal tissue. It has much more in common with conformal radiation therapy in terms of monitor units setup, scattered and leakage radiation and radiation to the normal tissue.

Online Interactive 3-D Virtual Views of Surface and Internal Anatomy and Functional Extent of Tumor Spread Incorporated Treatment Planning and Dose Calculations by Model Based Algorithms Using Convolution Superposition and Monte Carlo Methods Combined model based and Monte Carlo method of treatment planing and dose calculation (10) is more suitable for the method of 3-D virtual reality image guided radiation therapy and radiosurgery as described in this invention. The model based convolution superposition combined with Monte Carlo method of energy spectrum calculations gives better dose distribution calculations. The Monte Carlo method of dose calculation is more accurate method to determine the probability of distributions of individual interactions of photons and particles. However, it is difficult due to the need to calculate large number of such interactions. It used to take over eighteen hours or longer to complete such dose calculations.

With the present fast advancing computer and computation technology, the combined model based convolution superposition method and the Monte Carlo method can be performed in minutes. It allows its use as online fast and accurate dose calculations for the treatment planning. With a central supercomputer, such online treatment planning and dose calculation is made feasible for multiple centers simultaneously. It facilitates Telemedicine model shared online treatment planning and doses calculations during the radiation therapy and radiosurgery as in this invention.

Delivery of Radiation Therapy and Radiosurgery with the Aid of Interactive Views of Surface and Internal Anatomy by 3-D-CT or MRI Virtual Imaging After such single session simulation, treatment planning, field shaping block making and online interactive treatment planning, radiation therapy and radiosurgery is rendered to the patient who is already in treatment position on the accelerator's treatment table. The methods of patient's positioning on the treatment table were described before. The magnetic filed compatible imaging and treatment table 174 is equipped like a standard radiation therapy table that works with a Medical Accelerator.

In all filed simultaneous radiation therapy and radiosurgery method of treatment, the radiosurgical dose of 1000 cGy is rendered in 34.54 seconds if machine dose rate were 400 cGy and the tumor is treated by six-fields setup. If it were an eight-field, simultaneous treatment setup and the machine dose rate 400 cGy/min, then the 1,000 cGy radiosurgery is given in 25.9 seconds. If it were a six filed or an eight field setup daily intensity modulated radiation therapy (IMRT), and the machine dose rate were 400 cGy, then the beam on time to deliver 200 cGy to the tumor is only 5.18 or 6.9 seconds respectively. (Provisional Patent Application 60/872, 117 of Nov. 30, 2006, Lethal and Sublethal Damage Repair Inhibiting Image Guided Simultaneous All Field Divergent and Pencil Beam Photon and Electron Radiation Therapy and Radiosurgery). This treatment time is further decreased or increased based upon the machine dose rate. A patient can easily hold the breath for five to 35 seconds treatment time to eliminate the uncertainties associated with the organ movements.

Such short duration radiation therapy and radiosurgery facilitates efficient implementation of virtual reality 3-D-CT or CT-MRI image guided radiation therapy and radiosurgery with interactive views of surface and internal anatomy. It is almost like image guided surgery but in short duration and without the need for anesthesia in a difficult environment due to the presence of MRI magnet and with much improved safety to the patient. The average time for MRI image guided surgery is reported as 407 plus-minus 122 min which is 6.783 plus minus 2.383 hours (Canadian Journal of Anesthesia 49: 4, 420-426, 2002). In contrast, the MRI image guided radiosurgery could be completed in about half an hour to an hour. Most of this time is spent for patient setup with immobilization and imaging while the radiation dose delivery to the tumor itself as stated above takes only a few seconds. Most importantly, the functional integrity of the diseased organ is maintained with minimal or no compromise than it would be possible by surgery.

REFERENCES

1. U.S. Provisional Patent Application No. 60/790,192 filed on Apr. 6, 2006, Multiple Medical Accelerators and kV-CT Incorporated Radiation Therapy Device and Semi-Automated Custom Reshapeable Blocks for All Field Synchronous Image Guided 3-D Conformal-Intensity Modulated Radiation Therapy
2. Regular Patent Application Filed on Apr. 5, 2007, Multiple Medical Accelerators and kV-CT Incorporated Radiation Therapy Device and Semi-Automated Custom Reshapeable Blocks for All Field Synchronous Image Guided 3-D Conformal-Intensity Modulated Radiation Therapy
3. Provisional Application 60/872,117 of Nov. 30, 2006, Lethal and Sublethal Damage Repair Inhibiting Image Guided Simultaneous All Field Divergent and Pencil Beam Photon and Electron Radiation Therapy and Radiosurgery
4. Provisional Application 60/872,115 of Nov. 30, 2006 Lethal and Sublethal Damage Repair Inhibiting Image Guided Split Dose, Few Seconds Interval Divergent and Pencil Photon and Electron Radiation Beams Radiation
5. Disclosure Document 561105 filed on Sep. 14, 2004

6. Intraoperative mobile magnetic resonance imaging for craniotomy lengthens the procedure but does not increase morbidity: Canadian Journal of Anesthesia 49, 4: 420-426, 2002
7. Strassmann G, Braun I, Kress O, Richter D, Neidel H O, Klos K L, An H., Vogel B, Rose F and Engenhart-Cabilic R. Accuracy of Single Session Extracarnial Radiotherapy for Simple Shaped Tumor or Metastasis Using Fast 3-D CT Treatment Planning. Int J Radiat Oncol Biol Phys 2006; 60: 576-582
8. Wang B, Goldstein M, Xu X G and Sahoo N. Adjoint Monte Carlo Method for Prostate External Photon Beam Treatment Planning: An Application to 3D Patient Anatomy. Phys. Med. Biol. 2005; 50: 923-935
9. Textbook of Radiation Oncology, Radiosurgery, p 549-564, Dennis C. Shrive, David A. Larson and Jay S. Loeffler; ed. Steven A. Liebel and Theodore L. Phillips, 2004, Saunders
10. The Physics of Radiation Therapy, Three Dimensional Conformal Radiation Therapy, p 468-480, Faiz M. Khan, 2003, Lippencott Williams & Wilkins

What is claimed is:

1. A medical accelerator system for computerized tomography and magnetic resonance image guided radiation therapy and radiosurgery, wherein said radiation is rendered simultaneously to all treatment fields within a few seconds to less than a minute as intensity modulated radiation therapy with combined divergent and pencil beams or divergent or pencil beam alone.

2. A medical accelerator for image guided simultaneous radiation to all the treatment fields as in claim 1 for single session image guided radiation therapy simulation, field shaping block making, treatment planning, radiation therapy and radiosurgery.

3. A medical accelerator for image guided simultaneous radiation to all the treatment fields as in claim 1 wherein said accelerator is S-band, C-band or X-band linear accelerator and having variable megavoltage energies.

4. A medical accelerator for image guided simultaneous radiation to all the treatment fields as in claim 1 consisting of coplanar and non-coplanar beams from accelerator treatment heads placed in coplanar and non-coplanar plains.

5. A medical accelerator for image guided simultaneous radiation to all the treatment fields as in claim 1 for online interactive 3-D virtual views of surface and internal anatomy and functional extent of tumor spread incorporated treatment planning and dose calculations as with model based algorithms using convolution superposition and Monte Carlo methods.

6. A 3-D virtual reality interactive image guided online combined model based convolution superposition method and the Monte Carlo method of dose calculation and treatment planing in minutes as in claim 5 and said calculations are performed with a central supercomputer and is shared with other radiation oncology centers as Telemedicine model for shared online treatment planning and doses calculations during radiation therapy and radiosurgery.

7. A medical accelerator for image guided simultaneous radiation to all the treatment fields as in claim 1 wherein single medical accelerator heads are arranged in coplanar and non-coplanar planes for multiple field simultaneous radiation therapy and radiosurgery.

8. A medical accelerator for image guided simultaneous radiation to all the treatment fields as in claim 1 wherein single medical accelerators are arranged in coplanar and non-coplanar planes for multiple field simultaneous radiation therapy and radiosurgery.

9. A medical accelerator for image guided simultaneous radiation to all the treatment fields as in claim 1 wherein multiple beam accelerators are connected to beam lines that connects with single medical accelerator heads that renders coplanar beams and non-coplanar beams for multiple field simultaneous radiation therapy and radiosurgery.

10. A medical accelerator for image guided simultaneous radiation to all the treatment fields as in claim 1 wherein the imaging system contains the megavoltage computerized tomography.

11. A medical accelerator for image guided simultaneous radiation to all the treatment fields as in claim 1 wherein the imaging system contains the magnetic resonance imaging.

12. A medical accelerator for image guided simultaneous radiation to all the treatment fields as in claim 1 wherein the imaging system contains the functional imaging by magnetic resonance spectroscopy for online interactive views of tumor extension incorporated simulation, block making, treatment planning and radiation therapy and radiosurgery.

13. A medical accelerator for image guided simultaneous radiation to all the treatment fields as in claim 1 wherein the simulation, block making, treatment planning and radiation therapy and radiosurgery is rendered with interactive views of surface and internal anatomy by 3-D-CT and or MRI virtual imaging.

14. A medical accelerator for image guided simultaneous radiation to all the treatment fields as in claim 1 wherein intensity modulated radiation therapy to the entire 3-D-4-D tumor volume and its margins is rendered with conformal online image guided single session radiation therapy simulation, treatment planning computation.

15. A medical accelerator for image guided simultaneous radiation to all the treatment fields as in claim 1 wherein the gantry is fixed and non-rotating and the treatment head is equipped with scanning beams to render a few degree gantry rotational effect and beam's intensity modulation.

16. A medical accelerator for image guided simultaneous radiation to all the treatment fields as in claim 1 for super-high dose rate to tumor with lower machine dose rate to normal tissue.

17. A medical accelerator for image guided simultaneous radiation to all the treatment fields as in claim 1 for lower scattered and leakage radiation therapy and radiosurgery.

18. A medical accelerator for image guided simultaneous radiation to all the treatment fields as in claim 1 for radiation therapy and radiosurgery by only few seconds to less than a minute lasting exposure to radiation.

19. A medical accelerator system equipped with magnetic resonance image and computerized tomography for image-guided simultaneous coplanar and non-coplanar beam radiation therapy and radiosurgery that last only a few seconds to less than a minute radiation exposure to a tumor, wherein said radiation exposure is a super-high biological dose rate of about 1000-4000 cGy that inhibits lethal and sublethal damage repair, thereby bringing the relative biological effectiveness of photon and electron radiation closer to that of high Linear Energy Transfer radiation like that of proton and neutron.

20. An image guided, highly biologically effective radiation therapy system with coplanar and non-coplanar beams for radiation therapy and radiosurgery as in claim 19 for radiation therapy with lesser acute and late radiation toxicities including late occurring second primary tumors by keeping the radiation dose to normal tissue as very low.

21. An image guided, highly biologically effective radiation therapy system with coplanar and non-coplanar beams for radiation therapy and radiosurgery as in claim 19 to reduce acute and long term side effects of combined radiation therapy and chemotherapy including early and late developing hematological and pulmonary complications and late developing neurological damage and second primary tumors.

* * * * *